(12) United States Patent
Schertiger

(10) Patent No.: US 11,246,740 B2
(45) Date of Patent: Feb. 15, 2022

(54) ADHESIVE WAFER WITH RELEASE LINER

(71) Applicant: Coloplast A/S, Humlebaek (DK)

(72) Inventor: Lars Olav Schertiger, Fredensborg (DK)

(73) Assignee: Coloplast A/S, Humlebaek (DK)

(*) Notice: Subject to any disclaimer, the term of this patent is extended or adjusted under 35 U.S.C. 154(b) by 690 days.

(21) Appl. No.: 16/083,514

(22) PCT Filed: Mar. 10, 2017

(86) PCT No.: PCT/DK2017/050069
§ 371 (c)(1),
(2) Date: Sep. 10, 2018

(87) PCT Pub. No.: WO2017/152921
PCT Pub. Date: Sep. 14, 2017

(65) Prior Publication Data
US 2020/0163792 A1   May 28, 2020

(30) Foreign Application Priority Data

Mar. 11, 2016 (DK) .......................... PA 2016 70145

(51) Int. Cl.
*A61F 5/443* (2006.01)

(52) U.S. Cl.
CPC .................................... *A61F 5/443* (2013.01)

(58) Field of Classification Search
CPC .... A61F 5/443; A61F 5/445; A61F 13/00085; A61F 13/0259; A61F 2013/008
See application file for complete search history.

(56) References Cited

U.S. PATENT DOCUMENTS

| 4,890,608 | A | 1/1990 | Steer |
| 5,384,174 | A | 1/1995 | Ward et al. |
| 5,722,965 | A | 3/1998 | Kuczynski |
| 6,159,497 | A | 12/2000 | Laprade et al. |
| 6,641,910 | B1 | 11/2003 | Bries et al. |
| 9,248,214 | B2 | 2/2016 | Lykke et al. |
| 2007/0078418 | A1 | 4/2007 | May et al. |
| 2009/0299309 | A1* | 12/2009 | Fenton ..................... A61F 5/443 604/336 |
| 2010/0217215 | A1* | 8/2010 | Lykke ................... A61L 24/043 604/344 |

(Continued)

FOREIGN PATENT DOCUMENTS

| AU | 617789 A | 11/1989 |
| CA | 2398376 A1 | 7/2002 |

(Continued)

*Primary Examiner* — Nicholas J. Weiss
*Assistant Examiner* — Alessandro R Del Priore
(74) *Attorney, Agent, or Firm* — Coloplast Corp., Coloplast A/S; Nick Baumann

(57) ABSTRACT

An ostomy appliance comprising a wafer having an adhesive proximal side configured to be attached to a skin surface around an ostomy of a user and a distal side, a backing layer located on the distal side of the adhesive layer, a hole for accommodating a stoma. The adhesive side of the wafer is provided with a release liner, the release liner comprises frangible connections dividing the liner into segments that can be separately detached or the liner can be detached as a single unit.

13 Claims, 2 Drawing Sheets

(56) References Cited

U.S. PATENT DOCUMENTS

| | | | |
|---|---|---|---|
| 2011/0213321 A1* | 9/2011 | Fattman | A61F 5/448 604/344 |
| 2011/0213322 A1 | 9/2011 | Cramer et al. | |
| 2011/0245789 A1* | 10/2011 | Buus | A61F 5/445 604/344 |
| 2012/0189796 A1 | 7/2012 | Aoyagi et al. | |
| 2013/0090617 A1* | 4/2013 | Uveborn | A61F 5/443 604/344 |
| 2013/0138065 A1* | 5/2013 | Buus | A61F 5/443 604/344 |
| 2015/0073325 A1 | 3/2015 | Oeelund | |

FOREIGN PATENT DOCUMENTS

| | | |
|---|---|---|
| CN | 102227197 A | 10/2011 |
| CN | 104244879 A | 12/2014 |
| EP | 0793951 A1 | 9/1997 |
| GB | 2517680 A1 | 3/2015 |
| WO | 8911262 A1 | 11/1989 |
| WO | 10069326 A1 | 6/2010 |

* cited by examiner

ADHESIVE WAFER WITH RELEASE LINER

The invention relates to an ostomy appliance with a release liner.

SUMMARY OF THE INVENTION

One aspect of the disclosure provides an ostomy appliance in accordance with the appended claim 1.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated, as they become better understood by reference to the following detailed description. The elements of the drawings are not necessarily to scale relative to each other. Like reference numerals designate corresponding similar parts.

FIG. 3b is an enlarged view of a detail of FIG. 3a.

DETAILED DESCRIPTION

Figure 1:
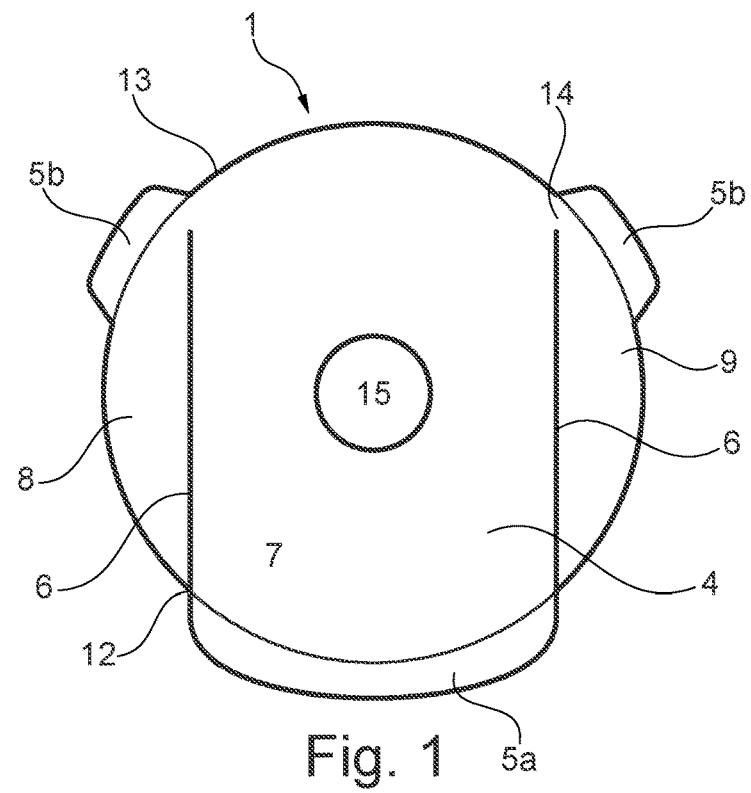
FIG. 1 is a plan view of one embodiment of an ostomy appliance.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

An axial direction is defined as the direction of the stoma, when the appliance is worn by a user. Thus, the axial direction is substantially perpendicular to a skin surface of a user, such as an abdominal skin surface. A radial direction is defined as transverse to the axial direction.

Prior to application to the skin a protective release liner covers the skin contacting side of the pressure sensitive adhesive body, in order to ensure that the properties of the adhesive are preserved and that the adhesive surface is not laid open until just before the use. The release liner is suitably a siliconised or fluorinated release liner, such as a siliconised or fluorinated craft paper, polyethylene, polypropylene or polyethylene terephthalate film. Suitably, the release liner is a siliconised polyethylene film, such as medium density polyethylene from the company Huhtamaki.

It is to be understood that the features of the various exemplary embodiments described herein may be combined with each other, unless specifically noted otherwise.

In the following, the words 'ostomy' and 'stoma' are used interchangeably without any intention to have different meanings.

Embodiments provide an ostomy appliance comprising a wafer having an adhesive proximal side configured to be attached to a skin surface around an ostomy of a user and a distal side, a backing layer located on the distal side of the adhesive layer, a hole for accommodating a stoma, the proximal adhesive side of the wafer comprises a central portion encirculating the hole and a peripheral portion encirculating the central portion and defining an outer rim of the wafer, a collection bag adapted to collect stomal output, a release liner covering the proximal adhesive side, wherein the release liner comprises one or more frangible connections which defines individual segments of the liner, wherein a major part of the frangible connections is in the form of weakened lines and a minor part of the frangible connections is in the form of unweakened lines.

By frangible connections is herein meant that the individual segments of the release liner are connected to define a single release liner, but the segments may be separated along the frangible connections if a force is applied.

In embodiments, the release liner comprises at least one frangible connection. In embodiments, each frangible connection is constituted of a weakened line and an unweakened line, arranged end to end.

In embodiments, the weakened lines are lines with reduced thickness compared to the thickness of the rest of the release liner. The release liner may have a uniform thickness apart from the weakened lines. The reduced thickness of the weakened lines enables easy tearing apart of the segments by the user.

The release liner may comprise any suitable material such as a polymer film or laminate. Examples of material may be polypropylene (PP) or A-PET amorphous polyethylene terephthalate. The release liner may have a thickness of 50-200 µm, such as 80-160 µm.

By the "thickness" of the release liner is meant the length of the shortest line which may be drawn between a specific point on the upper surface to a point on the bottom surface, or the shortest line which may be drawn between a specific point on the bottom surface to a point on the upper surface.

The size and outline of the release liner substantially corresponds to the size of the adhesive side of the wafer. Hence, the release liner has an outer rim substantially corresponding to the outer rim of the wafer.

The weakened lines may be produced by various methods. In embodiments, the weakened lines are made by kiss-cutting using a laser, hereby cutting partly through the material. In embodiments, the weakened lines are made by heat and/or pressure or scoring. In embodiments, the depths of the weakened lines are at least ⅓, such as ½ or even ⅔ of the thickness of the release liner.

In embodiments, the weakened lines may be cut from the proximal side of the release liner, thereby leaving the distal side of the release liner as a continuous layer.

By the distal side of the release liner being continuous is meant that the distal side of the release liner, being the side contacting the adhesive side of the wafer is uninterrupted. This facilitates that no marks may be made in the adhesive surface at the frangible connections. Such marks may occur during production on wafers with adjoining segments and cut-through of the release liner or they may appear through cold-flow of the adhesive during storage and the marks may constitute channels for leakage after application of the wafer.

In embodiments, the weakened line extends from a first side edge of the release liner and in a direction towards a second side edge of the release liner. The weakened lines may be linear or they may be curved. In embodiments, the extent of the weakened lines stop before reaching from the rim of the release liner at second side edge, thereby defining an unweakened line in the form of a continuous uninterrupted rim portion of the release liner at the second side edge of the release liner. In embodiments, the unweakened line of the frangible connection constitutes the part of the uninterrupted second edge portion extending from the weakened line to the rim of the release liner. This construction enables the user to remove the release liner one segment at the time if he peels it from the first side edge where the weakened line extends to the rim of the release liner. Peeling initiated at a weakened line and in a direction along the weakened line may lead to separation along the frangible connection and the segments of the release liner can thus be peeled separately from the adhesive side. When peeling has separated the segments along the entire weakened line, the unweakened line may be broken by application of a little extra force to completely separate the segments. When peeled from the second edge where the unweakened line extend to the edge and the edge portion thus is uninterrupted, the segments will stay connected and the entire release liner will be peeled off in one operation, as the frangible connections will not be broken during detachment of the release liner.

In embodiments, the frangible connection can be ruptured by application of a force when starting from the weakened line but not when starting from the unweakened line.

In embodiments, the length of the unweakened line, measured from the weakened line to the rim of the release liner is at least 0.3 mm, such as 0.5 mm, such as 0.7 mm, such as 1.0 mm or even at least 1.3 mm. The length of the unweakened line should be long enough to avoid the segments to separate unintentionally when the release liner is peeled starting from the unweakened line, but short enough to be easily torn apart when the release liner segments are peeled individually from the weakened line. In embodiments, the length of the unweakened line is less than 20 mm, such as 18 mm, such as 16 mm, such as 13 mm, such as 10 mm, such as 0.7 mm or even less than 0.5 mm.

A major part of the frangible connections is in the form of weakened lines whereas a minor part of the frangible connections is constituted by unweakened lines. By this is meant that the length of the weakened lines is substantially longer than the length of the unweakened lines. In embodiments, the weakened line has a length being at least 5 times the length of the unweakened line, such as 6, such as 7, such as 8, such as 9 or even such as at least 10 times the length of the unweakened line.

In embodiments, the weakened line at least partly defines a curved line circumferending the central part. Thus, a first segment may cover the central portion of the adhesive side, whereas a second segment may cover the peripheral portion of the adhesive side. A first radially weakened line defines a frangible connection between the first and the second segment. The second, peripheral segment may be provided with a second weakened line extending radially outwards from the first weakened line towards the rim of the release liner but stopping before the rim to provide an unweakened line from the second weakened line to the rim of the release liner.

In embodiments, a first segment of the release liner extends from one side edge to an opposed side edge of the release liner, covering at least a part of the central portion of the liner. The segment may cover a middle portion of the wafer, extending from a first side edge portion to a second side edge portion. In embodiments, opposed side edge portions may be covered with a second and a third segments.

In embodiments, the release liner may be provided with detachment means. Such detachment means may be in the form of and ear or tab extending radially away from the rim of the release liner or it may be other means enabling easy grabbing and detachment of the release liner such as a part with enlarged thickness. In embodiments, the liner may be provided with one or more detachment means. In embodiments, a detachment means is connected to each segment of the liner. The detachment means may be an integrated part of the release liner or the detachment means may be a separate part attached to the release liner. The detachment means may be visually marked for example by a colour to guide the user.

Embodiments provide a method of applying an ostomy appliance to the skin around a stoma comprising the steps of providing a wafer having an adhesive proximal side configured to be attached to a skin surface around an ostomy of a user and a distal side, a backing layer located on the distal side of the adhesive layer, a hole for accommodating a stoma, the proximal adhesive side of the wafer comprising a central portion encirculating the hole and a peripheral portion encirculating the central portion and defining an outer rim of the wafer, a collection bag adapted to collect stomal output, a release liner covering the proximal adhesive side, wherein the release liner comprises one or more frangible connections which defines individual segments of the liner, wherein a major part of the frangible connections is in the form of weakened lines and a minor part of the frangible connections is in the form of an unweakened lines, removing a first segment of the release liner, positioning the wafer around the stoma and applying the wafer to the skin around the stoma, removing the remaining segments of the release liner and bringing the entire adhesive side of the wafer in contact with the skin.

A collection bag may be attached to the wafer before or after application of the wafer or the collection bag may be integrated with the wafer.

Embodiments, and features of the various exemplary embodiments described in this application, may be combined with each other ("mixed and matched"), unless specifically noted otherwise.

DETAILED DESCRIPTION OF THE DRAWING

In the following detailed description, reference is made to the accompanying drawings. The drawings form a part of this specification and illustrate exemplary embodiments for practicing the invention. Directional terminology, such as "top," "bottom," "front," "back," "leading," "trailing," etc., is used with reference to the orientation of the Figure(s) being described. Because components of embodiments can be positioned in a number of orientations, the directional terminology is used for purposes of illustration and is in no way limiting. It is to be understood that other embodiments may be utilized and structural or logical changes may be made without departing from the scope of the invention. The detailed description describes examples for practicing the invention and is not to be read to limit the scope of the invention. The scope of the invention is defined by the attached claims.

FIG. 1 is a plan view of an embodiment seen from the skin-facing side. The wafer 1 comprises a backing layer 2 and an adhesive layer 3; the adhesive layer 2 is located on at least a part of the proximal side of the backing layer 2. A hole 15 for accommodating the stoma is provided. The proximal side of the adhesive layer 3 is covered with at least one release liner 4. The release liner 4 may optionally be provided with one or more ears 5a, 5b extending further radially outwards than the rim of the wafer and enabling easy grip of the release liner when detaching it from the adhesive side. The release liner 4 is provided with weakened lines 6 dividing the liner into segments 7, 8, 9. In FIG. 1 the release liner comprises three segments, a first middle segment 7 extending from a first edge 12 to a second edge 13 and covering the middle part of the wafer, and a second and a third side segments 8, 9 covering opposing side edge portions of the wafer. The weakened lines 6 extend from a first edge portion 12 towards a second edge portion 13, but the weakened line 6 stops shortly before the second edge portion 13 leaving the rim of the release liner along the second edge portion 13 with a continuous portion 14, with an unweakened line, where the release liner remains it thickness at the second edge portion 13,14.

The weakened lines 6 in the release liner may have a reduced thickness and thus is easy to separate by tearing the segments apart. If the segments 7, 8, 9 are pulled apart, starting from the first edge portion 12, the release liner may separate along the frangible connection.

The first middle and the edge release liners 7, 8, 9 are provided with ears 5a, 5b for easy detachment. When pulling the ear 5a of the first middle segment 7, the segment 7 will be torn apart from the side segments 8, 9 along the weakened line 6. When the segments 7, 8, 9 are separated along the entire weakened line 6, a minimum of force is required to tear the unweakened line 14 and thereby fully detach the first segment 7 from the wafer and from the other segments of the release liner. Then the wafer 1 can be positioned and applied around a stoma. When the wafer is positioned and partly adhered to the skin, the second and third side segments 8, 9 can be detached from the adhesive by pulling the ears 5b of the segments. This stepwise way of application enables the user to more precise positioning and handling of the wafer, which is especially advantageous when handling a soft or thin wafer.

However, if the user desires to remove the entire release liner 4 before initiating application, he may pull one of the ears 5b of the second side segment, and due to the unweakened line 14, the segments 7, 8, 9 will not separate, and the liner 4 can be detached as a single piece.

Figure 2:
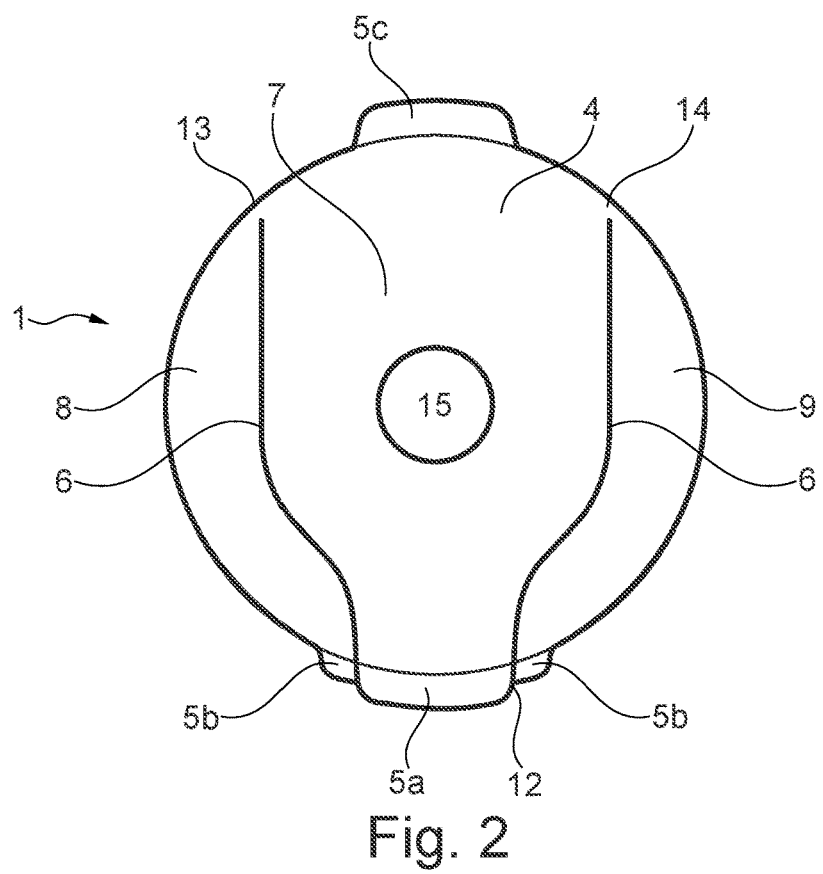
FIG. 2 is a plan view of another embodiment of an ostomy appliance.

In FIG. 2 is illustrated an embodiment of a wafer with a release liner comprising a first middle segment 7 and two side segments 8, 9 located on each side of the middle segment 7. The three segments 7, 8, 9 are all provided with an ear 5b at the first side edge portion 12. At the opposite, second edge portion 13 of the wafer, an ear 5c is also provided. When the ear 5c at the second edge portion 13 is pulled, the liner 4 is detached from the adhesive side in one piece. The coherence of the segments 7, 8, 9 along the unweakened line at the rim 14 facilitates that the release liner 4 comes off in one piece, as the weakened lines 6 are not exposed to tear forces due to the closed end (closed by the presence of the unweakened line) of the lines 6. The construction of the release liner enables the user to choose whether he will remove the entire liner at once and apply or, if he need more stability during application, for example if the wafer is thin and/or soft in texture, he can remove the first middle segment 7 first, position and apply the wafer to the skin and subsequently remove the side segments 8, 9.

Figure 3A:
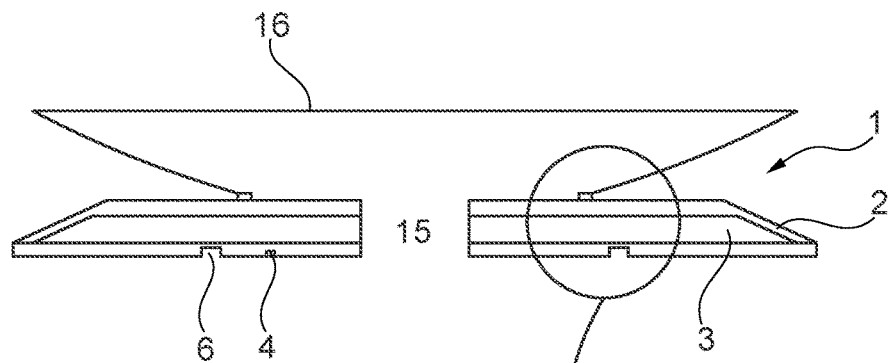
FIG. 3a is a cross-sectional side view of one embodiment of an ostomy appliance.
Figure 3B:
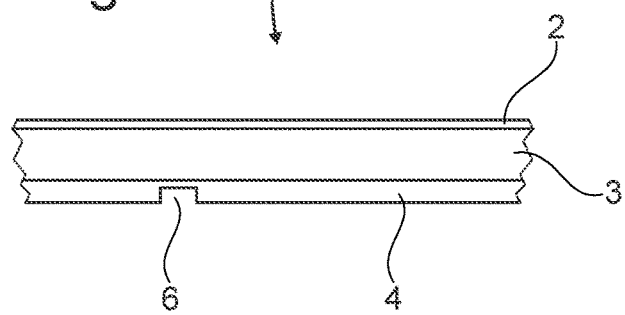

FIG. 3a shows a cross section view of an embodiment of an ostomy appliance. The appliance comprises a wafer 1 and a collection bag 16. The wafer comprises a backing layer 2 covered on the proximal side with an adhesive layer 3. The proximal adhesive side of the wafer is covered by a release liner 4. In FIG. 3b is shown an enlarged view of the area close to the weakened line 6, marked with a circle in FIG. 3a (the collection bag 16 is left out at FIG. 3b for simplicity). The weakened line 6 is in the form of a line of reduced thickness of the release liner 4. The distal side of the release liner may be continuous as the weakened line 6 is cut from the proximal side of the liner, leaving the distal side of the liner without cut through parts or lines. The advantage of this is that the surface of the release liner 4 contacting the adhesive 3 is unbroken and thus there will be little or no marks in the adhesive surface at the frangible connections between the segments of the release liner. Such marks may occur during production if the release liner is discontinuous or they may develop through cold-flow of the adhesive during storage and the marks may provide undesired channels for leakage after application of the wafer.

Figure 4:
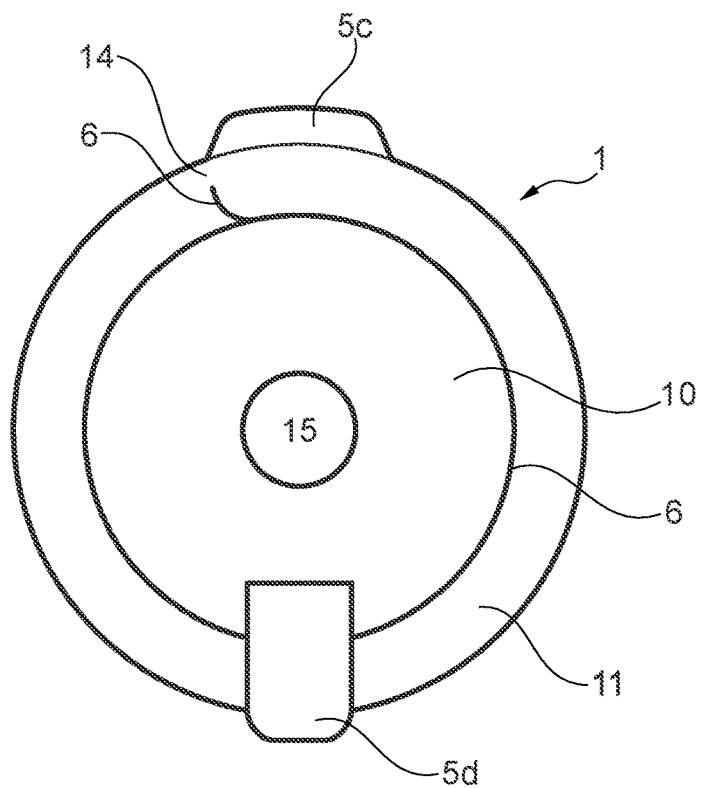
FIG. 4 is a plan view of a third embodiment of an ostomy appliance.

FIG. 4 illustrates an embodiment of a wafer comprising a release liner having a first segment 10 covering the central portion of the wafer. A second segment 11 of the release liner extends along the peripheral portion of the wafer. The first and the second segments are separated with a first weakened line 6 circumferending the central portion. The second peripheral segment 11 comprises a substantially radial frangible connection extending from the weakened line 6 circumferending the central portion and towards the rim of the release liner. This line stops before the rim of the release liner, leaving an unweakened line in the form of an uninterrupted portion 14 of the release liner along the edge portion. An ear 5c may be provided next to the area of the radially extending weakened line 6, the ear 5c extending radially from the edge of the release liner. The first central segment 10 may be provided with an ear 5d or tab attached next to the weakened line 6. The ear 5d or tab may be welded or adhered to the first segment. To apply the wafer, the first segment 10 is detached by pulling the ear 5d and thereby tearing the first segment 10 apart from the second segment 11 along the weakened line 6. The thus exposed central adhesive side is applied to the skin and then the second peripheral segment 11 is removed by pulling the ear 5c. At this stage of application, the central portion 10 of the adhesive side is adhered to the skin surrounding the stoma with a tack that may be higher than the force needed to break the uninterrupted edge portion 14 next to the ear 5c. Thus, the unweakened line will be torn open along the weakened line 6 and continuing along the unweakened line 14 to provide a radial separation, and the segment 11 can then be detached, and the wafer fully applied to the skin. If the user wish remove the entire release liner 4 before application, he may initiate the application of the wafer by pulling the ear 5c of the peripheral segment 11 and due to the unweakened line 14 the liner will come off in one piece, including the first central segment 10.

Embodiments, and features of the various exemplary embodiments described in this application, may be combined with each other ("mixed and matched"), unless specifically noted otherwise.

EXAMPLE

An ostomy wafer such as a Mio base plate from Coloplast A/S is provided with a 0.8 mm polypropylene release liner. The liner was scored by kiss-cutting by laser in a depth of ⅔ of the thickness of the liner to provide weakened lines. The weakened lines extend from the first edge of the liner towards the second opposite edge as shown in FIG. 1. The weakened lines stop before the second edge providing an unweakened line extending from the weakened line to the rim of the release. The liner is thereby divided into three segments and each of the segments are provided with an ear extending radially further than the periphery of the wafer. The segments are connected via easy tearable frangible connection lines.

The invention claimed is:

1. An ostomy appliance wafer comprising:
   a backing layer;
   an adhesive deposited on the backing layer, with a hole for accommodating a stoma formed through the adhesive and through the backing layer; and
   a release liner covering the adhesive;
   wherein the release liner comprises a mid-segment and a first frangible connection separating the mid-segment from a first segment of the release liner;
   wherein the release liner has a first thickness and the first frangible connection has a second thickness that is less than the first thickness;
   wherein the release liner has a rim located between a peripheral edge of the release liner and an end of the first frangible connection;
   wherein the release liner has a first ear connected to the mid-segment and a second ear connected to the rim, with the first ear and the second ear extending radially beyond the rim of the release liner;
   wherein the first frangible connection extends from the rim of the release liner from the first ear across a majority of the release liner and ends at a continuous portion of the release liner, with the continuous portion of the release liner provided with the first thickness and forming a continuous connection between the mid-segment and the first segment and the second ear;
   wherein the release liner is configured such that a first force applied to the first ear is adapted to separate the mid-segment away from the adhesive leaving the first segment covering the adhesive;
   wherein the continuous portion of the release liner is configured such that a second force applied to the second ear removes a remaining entirety of the release liner from the adhesive.

2. The ostomy appliance wafer of claim 1, wherein the first frangible connection is adapted to rupture by tearing in response to application of the first force.

3. The ostomy appliance wafer of claim 1, wherein a distal side of the release liner in contact with the adhesive is planar and continuous.

4. The ostomy appliance wafer of claim 1, wherein the mid-segment surrounds the hole.

5. The ostomy appliance wafer of claim 1, wherein the hole for accommodating the stoma is formed through the adhesive, the backing layer, and the mid-segment of the release liner.

6. The ostomy appliance wafer of claim 1, wherein the release liner comprises a second segment, with the first frangible connection separating the mid-segment and the first segment, and a second frangible connection separating the mid-segment and the second segment, and the continuous portion of release liner is configured such that the second force applied to the second ear removes the first segment and the second segment of the release liner from the adhesive.

7. The ostomy appliance wafer of claim 6, wherein the first force applied to the first ear separates the mid-segment away from the adhesive leaving the first segment and the second segment covering the adhesive.

8. The ostomy appliance wafer of claim 1, wherein the first frangible connection is curved to entirely surround the hole.

9. The ostomy appliance wafer of claim 1, further comprising a waste collection bag adapted for attachment to a distal side of the backing layer opposite the adhesive.

10. An ostomy appliance wafer comprising:
    an adhesive deposited between a backing layer and a release liner;
    wherein the release liner comprises a mid-segment connected to a first lateral segment by a first frangible connection and connected to a second lateral segment by a second frangible connection, wherein the release liner has a liner thickness and the first frangible connection and the second frangible connection each forms a weakened line of a thickness less than the liner thickness, with the mid-segment covering a center of the adhesive and the second lateral segment located on a side opposite from the first lateral segment;
    wherein the mid-segment includes a first ear that extends in a direction beyond an edge of the adhesive;
    wherein the first frangible connection extends from the first ear along a first side of the mid-segment toward a rim of the release liner, with a continuous portion of the release liner separating the first frangible connection from the rim a first offset distance;
    wherein the second frangible connection extends from the first ear along a second side of the mid-segment toward the rim of the release liner, with the continuous portion of the release liner further separating the second frangible connection from the rim by a second offset distance;
    wherein the first ear is coupled to both the first frangible connection and the second frangible connection;
    wherein the release liner has a second ear connected to the rim and a third ear connected to the rim, and the continuous portion of the release liner is provided with and maintains the liner thickness to continuously extend the release liner between the second ear and the third ear;
    wherein the release liner is configured such that a first force applied to the first ear is adapted to separate the mid-segment away from the adhesive leaving the first lateral segment and the second lateral segment covering the adhesive;
    wherein the continuous portion of the release liner is configured such that a second force applied to one of the second ear and the third ear of the release liner removes the first lateral segment and the second lateral segment of the release liner from the adhesive.

11. The ostomy appliance wafer of claim 10, wherein the second ear is connected to the first lateral segment and the mid-segment of the release liner.

12. The ostomy appliance wafer of claim 10, wherein the third ear is connected to the second lateral segment and the mid-segment of the release liner.

13. The ostomy appliance wafer of claim 10, wherein the continuous portion of the release liner continuously extends along the first lateral segment to the second ear, along a portion of the rim of the release liner across the mid-segment to the third ear, and along the second lateral segment.

\* \* \* \* \*